(12) United States Patent
Woodhouse et al.

(10) Patent No.: US 12,247,249 B2
(45) Date of Patent: **\*Mar. 11, 2025**

(54) METHOD FOR AMPLIFYING A GENOMIC SAMPLE

(71) Applicant: Inivata Ltd., Cambridge (GB)

(72) Inventors: Samuel Woodhouse, Cambridge (GB); Giovanni Marsico, Cambridge (GB); Vincent Plagnol, Cambridge (GB); Stefanie Lensing, Cambridge (GB)

(73) Assignee: INIVATA LTD., Cambridge (GB)

( * ) Notice: Subject to any disclaimer, the term of this patent is extended or adjusted under 35 U.S.C. 154(b) by 849 days.

This patent is subject to a terminal disclaimer.

(21) Appl. No.: 17/311,972

(22) PCT Filed: Dec. 17, 2019

(86) PCT No.: PCT/IB2019/060967
§ 371 (c)(1),
(2) Date: Jun. 8, 2021

(87) PCT Pub. No.: WO2020/128868
PCT Pub. Date: Jun. 25, 2020

(65) Prior Publication Data
US 2022/0056508 A1    Feb. 24, 2022

Related U.S. Application Data

(63) Continuation-in-part of application No. 16/230,609, filed on Dec. 21, 2018, now Pat. No. 10,533,214.

(51) Int. Cl.
*C12Q 1/6883* (2018.01)
*C12Q 1/6827* (2018.01)

(52) U.S. Cl.
CPC ......... *C12Q 1/6827* (2013.01); *C12Q 1/6883* (2013.01); *C12Q 2600/106* (2013.01); *C12Q 2600/156* (2013.01)

(58) Field of Classification Search
CPC .. C12Q 1/6827; C12Q 1/6883; C12Q 1/6886; C12Q 2600/106; C12Q 2600/156; C12Q 2600/16
See application file for complete search history.

(56) References Cited

U.S. PATENT DOCUMENTS 10,053,729 B2    8/2018  Vogelstein et al.
10,533,214 B2 *  1/2020  Woodhouse ......... C12Q 1/6827
(Continued)

OTHER PUBLICATIONS

Suyama et al., "MIG-seq: an effective PCR based method for genome-wide single-nucleotide polymorphism genotyping using the next generation sequencing platform," Scientific Reports, vol. 5, pp. 1-12. (Year: 2015).*

(Continued)

*Primary Examiner* — Angela M. Bertagna
*Assistant Examiner* — Francesca Filippa Giammona
(74) *Attorney, Agent, or Firm* — James S. Keddie; Bozicevic, Field & Francis LLP

(57) ABSTRACT

Provided herein is method for, among other things, estimating the number of sequence variations in a sample of DNA. In some embodiments, the method can be used to estimate the mutational load of a sample. In some embodiments, the method makes use of a set of primers that have 3' ends that specifically hybridizes to a sequence that is repeated multiple times in the genome. Thermocycling a reaction mix containing the primers may produce a reaction product comprising at least 50 amplicons having a total length of at least 100 kb. This product can be sequenced to provide an estimate of the number of sequence variations in the sample, and thus the mutational load of the sample.

15 Claims, 2 Drawing Sheets

Specification includes a Sequence Listing.

▶ = primer 1, which specifically hybridizes to repeated sequence in genome

→ = primer 2, which specifically hybridizes to repeated sequence in genome

(56) References Cited

U.S. PATENT DOCUMENTS

| | | | |
|---|---|---|---|
| 2012/0070832 A1 | 3/2012 | Green et al. | |
| 2012/0270739 A1* | 10/2012 | Rava | C12Q 1/6806 |
| | | | 702/20 |
| 2013/0060483 A1* | 3/2013 | Struble | G16B 20/20 |
| | | | 702/20 |
| 2017/0183731 A1* | 6/2017 | Mann | G16H 50/20 |

OTHER PUBLICATIONS

Suyama Supplementary Information. (Year: 2015).*

Takara Bio, "Multiplex PCR Assay Kit Ver.2," pp. 1-9. (Year: 2015).*

Allgäuer et al., "Implementing tumor mutational burden (TMB) analysis in routine diagnostics—a primer for molecular pathologists and clinicians", Transl Lung Cancer Res, 2018, 7(6):703-715.

Campesato et al., "Comprehensive cancer-gene panels can be used to estimate mutational load and predict clinical benefit to PD-1 blockade in clinical practice", Oncotarget, 2015, 6(33): 34221-34227.

Meléndez et al., "Methods of measurement for tumor mutational burden in tumor tissue", Transl Lung Cancer Res, 2018, 7(6):661-667.

Rizvi et al, "Mutational landscape determines sensitivity to PD-1 blockade in non-small cell lung cancer", Science, 2015, 348(6230): 124-128. doi:10.1126/science.aaa1348.

Belic et al., "Rapid Identification of Plasma DNA Samples with Increased ctDNA Levels by a Modified FAST-SeqS Approach", Clinical Chemistry, 2015, 61:6, pp. 838-849.

Buttner et al., "Implementing TMB measurement in clinical practice: considerations on assay requirements", ESMO Open, 2019, 4:e000442, pp. 1-12.

Elazezy et al., "Techniques of using circulating tumor DNA as a liquid biopsy component in cancer management", Computational and Structural Biotechnology Journal, 2018, 16: 370-378.

Kinde et al., "FAST-SeqS: A Simple and Efficient Method for the Detection of Aneuploidy by Massively Parallel Sequencing", PLoS ONE, 2012, 7(7): e41162, pp. 1-8.

Kinde et al., "FAST-SeqS: A Simple and Efficient Method for the Detection of Aneuploidy by Massively Parallel Sequencing", PLoS ONE, 2012, 7(7): e41162, suppl. Table S2.

Li et al., "Development of Three Multiplex PCR Primer Sets for Ark Shell (*Scapharca broughtonii*) and Their Validation in Parentage Assignment", J. Ocean Univ. China, 2016, 15(2): 311-317.

Palmirotta et al., "Liquid biopsy of cancer: a multimodal diagnostic tool in clinical oncology", Therapeutic Advances in Medical Oncology, 2018, 10: 1-24.

Wang et al., "Selection and development of representative simple sequence repeat primers and multiplex SSR sets for high throughput automated genotyping in maize", Chinese Science Bulletin, 2007, 52(2): 215-223.

Weising et al., "A set of conserved PCR primers for the analysis of simple sequence repeat polymorphisms in chloroplast genomes of dicotyledonous angiosperms", Genome, 1999, 42: 9-19.

American Cancer Society, "Immune checkpoint inhibitors to treat cancer", downloaded from www.cancer.org/treatment/treatments-and-side-effects/treatment-types/immunotherapy/immune-checkpoint-inhibitors.html, 2018, pp. 1-2.

* cited by examiner

= primer 1, which specifically hybridizes to repeated sequence in genome

= primer 2, which specifically hybridizes to repeated sequence in genome

SEQUENCE LISTING

<160> NUMBER OF SEQ ID NOS: 34

<210> SEQ ID NO 1
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 1
tcgtcggcag cgtcagatgt gtataagaga cagagcctcc caagtagctg g          51

<210> SEQ ID NO 2
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 2
tcgtcggcag cgtcagatgt gtataagaga cagcactgca ctccagcctg g          51

<210> SEQ ID NO 3
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 3
tcgtcggcag cgtcagatgt gtataagaga cagcattgca ctccagcctg g          51

<210> SEQ ID NO 4
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 4
tcgtcggcag cgtcagatgt gtataagaga cagcccacct cagcctccca a          51

<210> SEQ ID NO 5
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 5
tcgtcggcag cgtcagatgt gtataagaga cagctcagcc tcccaaagtg c          51

<210> SEQ ID NO 6
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 6
tcgtcggcag cgtcagatgt gtataagaga cagggaggcg gaggttgcag t          51

<210> SEQ ID NO 7
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 7
tcgtcggcag cgtcagatgt gtataagaga cagggaggtt gcagtgagcc g          51

<210> SEQ ID NO 8

-continued

<210> SEQ ID NO 8
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 8
tcgtcggcag cgtcagatgt gtataagaga cagtacaggc atgagccacc g        51

<210> SEQ ID NO 9
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 9
tcgtcggcag cgtcagatgt gtataagaga cagtggaggt tgcagtgagc c        51

<210> SEQ ID NO 10
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 10
gtctcgtggg ctcggagatg tgtataagag acagagcctc ccaagtagct gg       52

<210> SEQ ID NO 11
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 11
gtctcgtggg ctcggagatg tgtataagag acagcactgc actccagcct gg       52

<210> SEQ ID NO 12
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 12
gtctcgtggg ctcggagatg tgtataagag acagcattgc actccagcct gg       52

<210> SEQ ID NO 13
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 13
gtctcgtggg ctcggagatg tgtataagag acagcccacc tcagcctccc aa       52

<210> SEQ ID NO 14
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 14
gtctcgtggg ctcggagatg tgtataagag acagctcagc ctcccaaagt gc          52

<210> SEQ ID NO 15
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 15
gtctcgtggg ctcggagatg tgtataagag acagggaggc ggaggttgca gt          52

<210> SEQ ID NO 16
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 16
gtctcgtggg ctcggagatg tgtataagag acagggaggt tgcagtgagc cg          52

<210> SEQ ID NO 17
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 17
gtctcgtggg ctcggagatg tgtataagag acagtacagg catgagccac cg          52

<210> SEQ ID NO 18
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 18
gtctcgtggg ctcggagatg tgtataagag acagtggagg ttgcagtgag cc          52

<210> SEQ ID NO 19
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 19
aatgatacgg cgaccaccga gatctacacc tctctattcg tcggcagcgt c           51

<210> SEQ ID NO 20
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 20
aatgatacgg cgaccaccga gatctacact atcctcttcg tcggcagcgt c           51

<210> SEQ ID NO 21
<211> LENGTH: 51
<212> TYPE: DNA

<213> ORGANISM: Artificial sequence
<220> FEATURE:
<223> OTHER INFORMATION: synthetic oligonucleotide

<400> SEQUENCE: 21
aatgatacgg cgaccaccga gatctacacg taaggagtcg tcggcagcgt c    51

<210> SEQ ID NO 22
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 22
aatgatacgg cgaccaccga gatctacaca ctgcatatcg tcggcagcgt c    51

<210> SEQ ID NO 23
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 23
aatgatacgg cgaccaccga gatctacaca aggagtatcg tcggcagcgt c    51

<210> SEQ ID NO 24
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 24
aatgatacgg cgaccaccga gatctacacc taagccttcg tcggcagcgt c    51

<210> SEQ ID NO 25
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 25
aatgatacgg cgaccaccga gatctacacc gtctaattcg tcggcagcgt c    51

<210> SEQ ID NO 26
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 26
aatgatacgg cgaccaccga gatctacact ctctccgtcg tcggcagcgt c    51

<210> SEQ ID NO 27
<211> LENGTH: 47
<212> TYPE: DNA
<213> ORGANISM: Artificial sequence
<220> FEATURE:
<223> OTHER INFORMATION: synthetic oligonucleotide

<400> SEQUENCE: 27
caagcagaag acggcatacg agattcgcct tagtctcgtg ggctcgg    47

<210> SEQ ID NO 28
<211> LENGTH: 47
<212> TYPE: DNA
<213> ORGANISM: Artificial sequence
<220> FEATURE:
<223> OTHER INFORMATION: synthetic oligonucleotide

<400> SEQUENCE: 28
caagcagaag acggcatacg agatctagta cggtctcgtg ggctcgg        47

<210> SEQ ID NO 29
<211> LENGTH: 47
<212> TYPE: DNA
<213> ORGANISM: Artificial sequence
<220> FEATURE:
<223> OTHER INFORMATION: synthetic oligonucleotide

<400> SEQUENCE: 29
caagcagaag acggcatacg agatttctgc ctgtctcgtg ggctcgg        47

<210> SEQ ID NO 30
<211> LENGTH: 47
<212> TYPE: DNA
<213> ORGANISM: Artificial sequence
<220> FEATURE:
<223> OTHER INFORMATION: synthetic oligonucleotide

<400> SEQUENCE: 30
caagcagaag acggcatacg agatgctcag gagtctcgtg ggctcgg        47

<210> SEQ ID NO 31
<211> LENGTH: 47
<212> TYPE: DNA
<213> ORGANISM: Artificial sequence
<220> FEATURE:
<223> OTHER INFORMATION: synthetic oligonucleotide

<400> SEQUENCE: 31
caagcagaag acggcatacg agataggagt ccgtctcgtg ggctcgg        47

<210> SEQ ID NO 32
<211> LENGTH: 47
<212> TYPE: DNA
<213> ORGANISM: Artificial sequence
<220> FEATURE:
<223> OTHER INFORMATION: synthetic oligonucleotide

<400> SEQUENCE: 32
caagcagaag acggcatacg agatcatgcc tagtctcgtg ggctcgg        47

<210> SEQ ID NO 33
<211> LENGTH: 47
<212> TYPE: DNA
<213> ORGANISM: Artificial sequence
<220> FEATURE:
<223> OTHER INFORMATION: synthetic oligonucleotide

<400> SEQUENCE: 33
caagcagaag acggcatacg agatgtagag aggtctcgtg ggctcgg        47

<210> SEQ ID NO 34
<211> LENGTH: 47
<212> TYPE: DNA
<213> ORGANISM: Artificial sequence
<220> FEATURE:

```
<223> OTHER INFORMATION: synthetic oligonucleotide

<400> SEQUENCE: 34
caagcagaag acggcatacg agatcagcct cggtctcgtg ggctcgg                47
```

METHOD FOR AMPLIFYING A GENOMIC SAMPLE

CROSS-REFERENCING

This application is a § 371 national phase of International Application No. PCT/IB2019/060967, filed on Dec. 17, 2019, which claims the benefit of U.S. non-provisional application Ser. No. 16/230,609, filed on Dec. 21, 2018, now issued as U.S. Pat. No. 10,533,214, which applications are incorporated by reference in their entireties.

SEQUENCE LISTING

A Sequence Listing is provided as a text file entitled "INIV-006US_SEQ_LIST_ST25", created on Oct. 25, 2021, and having a size of 7,173 bytes. The contents of the text file are incorporated by reference herein in their entirety.

BACKGROUND

Immunotherapy represents one of the promising approaches for the treatment of cancer. In this approach, a patient's immune system is recruited to fight against tumor development and growth. The most successful immunotherapeutics to date have been immune checkpoint inhibitors, including antibodies that bind to programmed cell death protein 1 (PD-1), PD-L1, or CTLA-4.

The efficacy of immunotherapy has been demonstrated in several studies. However, such treatment is only effective in in a subset of patients. As such, there is currently an intense effort to develop methods for identifying patients that are likely to respond to immunotherapeutic drugs.

Rizvi et al (Mutational landscape determines sensitivity to PD-1 blockade in non-small cell lung cancer. Science 2015 348: 124-128) shows that the mutation load of a tumor (i.e., the number of nonsynonymous point mutations associated with the tumor), can be predictive for treatment response. Rizvi performed whole exome sequencing of non-small cell lung cancers treated with pembrolizumab, an antibody targeting programmed cell death-1 (PD-1), and showed that an increase in the number of nonsynonymous point mutations associated with a tumor (i.e., an increase in tumor mutation load) correlates with improved objective response, durable clinical benefit (DCB), and progression-free survival (PFS).

Measuring the mutational load of a tumor is challenging because: i. mutations are relatively rare events, even in the genome of a cancer cell and ii. samples of DNA from a patient carrying a tumor typically contain a mixture of DNA from the tumor and DNA that is not from the tumor. The latter is particularly problematic for cell-free DNA, which may contain as little as 1% to 10% of DNA from the tumor. As such, in order to measure the mutational load of a tumor, a significant portion, e.g., at least a few hundred kb or more than a Mb, of the genome should be sequenced at a read depth that is sufficient to identify mutations that may only be present at a relatively low frequency (e.g., 1%-10%) in the sample. Mutational load has been estimated using whole-exome sequencing (Rizvi, supra) and by sequencing panels of hundreds of selected cancer-related genes (see, e.g., Campesato, et al. Oncotarget 2015 6: 34221-34227). These methods require enriching regions of the genome (e.g., exons or cancer-related sequences) using hybridization/bait based technologies, and then sequencing the enriched regions. Such methods are multi-step, costly, inefficient and not readily implementable in a high throughput manner.

PCR strategies are generally not used to measure tumor mutational load because, at best, PCR is only able to amplify a few tens of kb of a genome, even in a multiplex PCR reaction. This length is generally insufficient to provide an estimate of mutation load. This problem is compounded by the fact that many of the most accessible patient samples (e.g., liquid biopsies and the like) contain DNA that is highly fragmented, making it impossible to amplify longer fragments.

Better methods for estimating tumor mutational load are therefore needed.

SUMMARY

Provided herein is a method for amplifying a sample. In some embodiments the method may comprise: (a) combining a sample of DNA with a thermostable polymerase, dNTPs and a set of at least 10 primers to produce a reaction mix, wherein: i. the 3' end of each primer specifically hybridizes to a sequence that is repeated at least 20 times in a eukaryotic genome, and ii. collectively, the set of primers amplifies at least 50 regions having a total length of at least 100 kb, in a polymerase chain reaction using the eukaryotic genome as a template; and (b) subjecting the reaction mix to thermocycling to produce a reaction product comprising at least 50 amplicons having a total length of at least 100 kb.

In some embodiments, the method may be used to estimate the number of sequence variations in a sample of DNA. The sequence variations can be mutations and, as such, the method can be used to estimate the mutational load of a sample. In some embodiments, the method may comprise (a) combining the sample of DNA with a thermostable polymerase, dNTPs and a set of primers to produce a reaction mix, wherein the 3' end of each primer specifically hybridizes to a sequence that is repeated multiple times in the genome of the subject from whom the sample was obtained; (b) thermocycling the reaction mix to produce a reaction product comprising at least 50 amplicons having a total length of at least 100 kb; (c) sequencing the amplicons or amplification products thereof to produce sequence reads; and (d) analyzing the sequence reads to estimate the number of sequence variations in the amplified regions. In this method, the number of sequence variations identified in step (d) provides an estimate of the number of sequence variations in the sample.

In some embodiments, the method may be used for copy number analysis and, as such, may be used to detect fetal aneuploidy or cancer specific changes. It may also be used to assess the level of known variants for example tracking polymorphisms to monitor organ transplants. Depending on context the term "copy number" can refer to the copy number of a particular region or entire chromosome (e.g., in the case of an aneuploidy or a duplication/amplification of a specific region) or the amount of a foreign genome in the cfDNA (e.g., in the case organ transplants).

The 3' ends of the primers used in the present method each hybridize to a sequence that is repeated multiple times (e.g., at least 20 times, at least 50 times, at least 100 times, at least 500 times, at least 1,000 times, at least 5,000 times or at least 10,000 times) in the genome of the subject under study. These are not "random" primers and neither do they require degenerate bases at their 3' ends. Rather, each of the primers has a known, predetermined, sequence of nucleotides at the 3' end (in most cases a sequence of at least 10, at least 12 nucleotides, at least 15 nucleotides or at least 18 nucleotides), that has been specifically designed to hybridize to a single, complementary sequence, where the sequence is repeated (i.e., found multiple times) in the genome. Thus, unlike traditional PCR, which requires primers that hybridize to and primer DNA synthesis at sites that are only found once (i.e., "unique sites") in a genome, the primers used in the present method have been deliberately designed to bind and prime DNA synthesis at multiple sites in the genome.

While each primer binds to multiple sites in the genome, only primers that bind to proximal sites on opposite strands with their 3' ends pointing towards each other (i.e., primers that bind to "opposing sites") will generate amplicons in a polymerase chain reaction. As such, many more amplicons can be generated than the number of primers used. For example, depending on how the primers are designed and their number, an amplification reaction that uses less than 100 primers can generate thousands or tens of thousands of discrete, non-overlapping, amplicons that, collectively, can include at least 100 kb, at least 1 Mb or at least at least 5 Mb of the genome. This principle is illustrated in FIG. 1, which is described in greater detail below. As noted below, the number of amplicons produced can be many times the number of primers used. This is in contrast to conventional PCR in which the number of amplicons produced is generally less than the number of primers used.

The number and the length of the amplicons produced using a set of primers can be predicted in silico and altered by, for example, adding or reducing the number of primers in the set, or using different primers. The minimal length of the amplicons produced by the reaction can be altered by, for example, mapping the primers to a reference sequence of the genome and eliminating a primer if it binds to a site that is too "close" to a binding site for another primer on the opposite strand. Illustrated by example, eliminating primers that bind less than 100 nt from an opposing primer will result in amplicons that are at least 100 nucleotides in length (excluding the primer sequences themselves). Likewise, eliminating primers that bind less than 500 nt from an opposing primer will result in amplicons that are at least 500 nucleotides in length (excluding the primer sequences themselves).

In addition to altering the primer composition, the median length and upper limit of the amplicons produced in a PCR reaction can be increased or decreased by, for example, altering the PCR conditions, e.g., by increasing or decreasing the length of extension cycle of the PCR. For example, use of a relative short extension cycle (e.g., from 10s to 30s) would favor the production of shorter amplicons over longer amplicons, and use of a relative long extension cycle (e.g., from 1 min to 5 mins) would allow longer amplicons to be produced in addition to the shorter amplicons. Finally, the median length and upper limit of the amplicons produced in a PCR reaction using the primers can also be imposed by the template. Specifically, in theory it should be impossible to produce an amplicon that is longer than any of the fragments in the template and, as such, use of a DNA sample that contains smaller fragments should result in smaller amplicons. For example, performing the present method on cfDNA isolated from the bloodstream of a subject should result in amplicons that have a median length of less than 500 bp (e.g., in the range of 100 to 500 bp), where at least 95% of the amplicons are below 400 bp in length.

Depending on how the method is implemented, the method may have certain advantages over conventional methods. In particular, because the method is PCR-based it can potentially be done by simply adding a DNA template to a reaction mix, thermocycling the reaction mix, and then directly sequencing the PCR products (or an amplification product thereof) e.g., on an Illumina sequencer. In some cases, as with other library preparation protocols, the initial PCR products may themselves be amplified with a set of primers that add sequencing platform-specific 5' tails prior to sequencing. Thus, the method can be readily integrated into many high throughput next-generation sequencing workflows. Using the present method, amplicons representing several hundred kb or Mb of a genome can be generated in a single PCR reaction (e.g., a reaction that contains 10-100 primers), thereby making it possible to analyze the mutation load of a sample without the added complications associated with enriching for specific sequences by hybridization to bait molecules.

These and other advantages may become apparent in view of the following disclosure.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
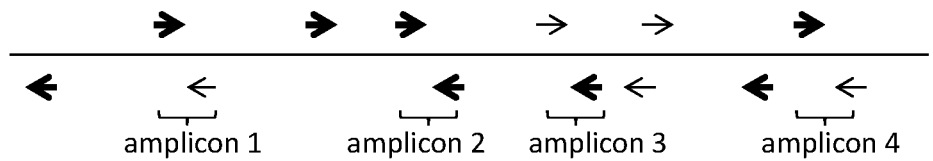
FIG. 1 schematically illustrates a principle of the present method, namely how use of primers that hybridize to a repeated sequence in a polymerase chain reaction can result in many more amplicons than the number of primers used. In the example, use of two primers that each hybridizes to multiple sites in a chromosomal region results in four amplicons. When an entire genome is used as a template, hundreds, thousands or tens of thousands of regions of the genome can be are amplified, particularly if more primers are used.

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, greater than 10,000 bases, greater than 100,000 bases, greater than about 1,000,000, up to about $10^{10}$ or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "nucleic acid sample," as used herein, denotes a sample containing nucleic acids. Nucleic acid samples used herein may be complex in that they contain multiple different molecules that contain sequences. Genomic DNA samples from a mammal (e.g., mouse or human) are types of complex samples. Complex samples may have more than about $10^4$, $10^5$, $10^6$ or $10^7$, $10^8$, $10^9$ or $10^{10}$ different nucleic acid molecules. Any sample containing nucleic acid, e.g., genomic DNA from tissue culture cells or a sample of tissue, may be employed herein.

The term "oligonucleotide" as used herein denotes a multimer of nucleotides of about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers are extended by a DNA polymerase. Primers are generally of a length compatible with their use in synthesis of primer extension products, and are usually in the range of 8 to 200 nucleotides in length, such as 10 to 100 or 15 to 80 nucleotides in length. A primer may contain a 5' tail that does not hybridize to the template. Primers are usually single-stranded for maximum efficiency in amplification, but may alternatively be double-stranded or partially double-stranded. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a region of nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strand region in a hybridization reaction. The hybridization reaction can be made to be highly specific by adjustment of the hybridization conditions under which the hybridization reaction takes place, such that two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.).

The term "duplex," or "duplexed," as used herein, describes two complementary polynucleotide region that are base-paired, i.e., hybridized together.

"Genetic locus," "locus,", "locus of interest", "region" or "segment" in reference to a genome or target polynucleotide, means a contiguous sub-region or segment of the genome or target polynucleotide. As used herein, genetic locus, locus, or locus of interest may refer to the position of a nucleotide, a gene or a portion of a gene in a genome or it may refer to any contiguous portion of genomic sequence whether or not it is within, or associated with, a gene, e.g., a coding sequence. A genetic locus, locus, or locus of interest can be from a single nucleotide to a segment of a few hundred or a few thousand nucleotides in length or more. In general, a locus of interest will have a reference sequence associated with it (see description of "reference sequence" below).

The term "reference sequence", as used herein, refers to a known nucleotide sequence, e.g. a chromosomal region or genome whose sequence is deposited at NCBI's Genbank database or other databases, for example. A reference sequence can be a wild type sequence.

The terms "plurality", "population" and "collection" are used interchangeably to refer to something that contains at least 2 members. In certain cases, a plurality, population or collection may have at least 10, at least 100, at least 1,000, at least 10,000, at least 100,000, at least $10^6$, at least $10^7$, at least $10^8$ or at least $10^9$ or more members.

The term "variable", in the context of two or more nucleic acid sequences that are variable, refers to two or more nucleic acids that have different sequences of nucleotides relative to one another. In other words, if the polynucleotides of a population have a variable sequence, then the nucleotide sequence of the polynucleotide molecules of the population may vary from molecule to molecule. The term "variable" is not to be read to require that every molecule in a population has a different sequence to the other molecules in a population.

The term "sequence variation", as used herein, is a variant that is present a frequency of less than 50%, relative to other molecules in the sample, where the other molecules in the sample are substantially identical to the molecules that contain the sequence variation. In some cases, a particular sequence variation may be present in a sample at a frequency of less than 20%, less than 10%, less than 5%, less than 1% or less than 0.5%. A sequence variation may be generated somatic mutation. However, in other embodiments, sequence variation may be derived from a developing fetus, a SNP or an organ transplant, for example.

The term "nucleic acid template" is intended to refer to the initial nucleic acid molecule that is copied during amplification. Copying in this context can include the formation of the complement of a particular single-stranded nucleic acid. The "initial" nucleic acid can comprise nucleic acids that have already been processed, e.g., amplified, extended, labeled with adaptors, etc.

The term "tailed", in the context of a tailed primer or a primer that has a 5' tail, refers to a primer that has a region (e.g., a region of at least 12-50 nucleotides) at its 5' end that does not hybridize or partially hybridizes to the same target as the 3' end of the primer.

The term "initial template" refers to a sample that contains a target sequence to be amplified. The term "amplifying" as used herein refers to generating one or more copies of a target nucleic acid, using the target nucleic acid as a template.

A "polymerase chain reaction" or "PCR" is an enzymatic reaction in which a specific template DNA is amplified using one or more pairs of sequence specific primers.

"PCR conditions" are the conditions in which PCR is performed, and include the presence of reagents (e.g., nucleotides, buffer, polymerase, etc.) as well as temperature cycling (e.g., through cycles of temperatures suitable for denaturation, renaturation and extension), as is known in the art.

The term "unique sequence-specific primer" as used herein refers to a primer that only binds to and extends at a unique site in a sample under study. The primers used herein do not unique bind to a unique sequence. However, they are sequence-specific.

The term "next generation sequencing" refers to the so-called highly parallelized methods of performing nucleic acid sequencing and comprises the sequencing-by-synthesis or sequencing-by-ligation platforms currently employed by Illumina, Life Technologies, Pacific Biosciences and Roche, etc. Next generation sequencing methods may also include, but not be limited to, nanopore sequencing methods such as offered by Oxford Nanopore or electronic detection-based methods such as the Ion Torrent technology commercialized by Life Technologies.

The term "sequence read" refers to the output of a sequencer. A sequence read typically contains a string of Gs, As, Ts and Cs, of 50-1000 or more bases in length and, in many cases, each base of a sequence read may be associated with a score indicating the quality of the base call.

The terms "assessing the presence of" and "evaluating the presence of" include any form of measurement, including determining if an element is present and estimating the amount of the element. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent.

If two nucleic acids are "complementary," they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "extending", as used herein, refers to the extension of a primer by the addition of nucleotides using a polymerase. If a primer that is annealed to a nucleic acid is extended, the nucleic acid acts as a template for extension reaction.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

As used herein, the terms "cell-free DNA from the bloodstream" "circulating cell-free DNA" and cell-free DNA" ("cfDNA") refers to DNA that is circulating in the peripheral blood of a patient. The DNA molecules in cell-free DNA may have a median size that is below 1 kb (e.g., in the range of 50 bp to 500 bp, 80 bp to 400 bp, or 100-1,000 bp), although fragments having a median size outside of this range may be present. Cell-free DNA may contain circulating tumor DNA (ctDNA), i.e., tumor DNA circulating freely in the blood of a cancer patient or circulating fetal DNA (if the subject is a pregnant female). cfDNA can be obtained by centrifuging whole blood to remove all cells, and then isolating the DNA from the remaining plasma or serum. Such methods are well known (see, e.g., Lo et al, Am J Hum Genet 1998; 62:768-75). Circulating cell-free DNA can be double-stranded or single-stranded. This term is intended to encompass free DNA molecules that are circulating in the bloodstream as well as DNA molecules that are present in extra-cellular vesicles (such as exosomes) that are circulating in the bloodstream.

As used herein, the term "circulating tumor DNA" (or "ctDNA") is tumor-derived DNA that is circulating in the peripheral blood of a patient. ctDNA is of tumor origin and originates directly from the tumor or from circulating tumor cells (CTCs), which are viable, intact tumor cells that shed from primary tumors and enter the bloodstream or lymphatic system. The precise mechanism of ctDNA release is unclear, although it is postulated to involve apoptosis and necrosis from dying cells, or active release from viable tumor cells. ctDNA can be highly fragmented and in some cases can have a mean fragment size about 100-250 bp, e.g., 150 to 200 bp long. The amount of ctDNA in a sample of circulating cell-free DNA isolated from a cancer patient varies greatly: typical samples contain less than 10% ctDNA, although many samples have less than 1% ctDNA and some samples have over 10% ctDNA. Molecules of ctDNA can be often identified because they contain tumorigenic mutations.

As used herein, the term "sequence variation" refers to the combination of a position and type of a sequence alteration. For example, a sequence variation can be referred to by the position of the variation and which type of substitution (e.g., G to A, G to T, G to C, A to G, etc. or insertion/deletion of a G, A, T or C, etc.) is present at the position. A sequence variation may be a substitution, deletion, insertion or rearrangement of one or more nucleotides. In the context of the present method, a sequence variation can be generated by a genetic variation.

As used herein, the term "genetic variation" refers to a variation (e.g., a nucleotide substitution, an indel or a rearrangement) that is present or deemed as being likely to be present in a nucleic acid sample. A genetic variation can be from any source. For example, a genetic variation can be generated by a mutation (e.g., a somatic mutation), an organ transplant or pregnancy. If sequence variation is called as a genetic variation, the call indicates that the sample likely contains the variation; in some cases a "call" can be incorrect. In many cases, the term "genetic variation" can be replaced by the term "mutation". For example, if the method is being uses to detect sequence variations that are associated with cancer or other diseases that are caused by mutations, then "genetic variation" can be replaced by the term "mutation".

As used herein, the term "calling" means indicating whether a particular sequence variation is present in a sample. This may involve, for example, providing a sequence that contains the sequence variation and/or annotating a sequence having the sequence variation, indicating that the sequence has an A to T variation at a specific position.

The term "amplicon" refers to a region of a genome that has been amplified by PCR. The number and sequences of a plurality of amplified regions should be the same as the number and sequences of the resulting amplicons. Thus, the terms "amplified regions" and "amplicons" can refer to the same thing.

As used herein, the term "value" refers to a number, letter, word (e.g., "high", "medium" or "low") or descriptor (e.g., "+++" or "++"). A value can contain one component (e.g., a single number) or more than one component, depending on how a value is analyzed.

Other definitions of terms may appear throughout the specification. It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As noted above, some embodiments of the method make use of a set of primers (e.g., at least 10, at least 20, at least 50, up to 100 or more primers), where the 3' end of each primer specifically hybridizes to a sequence that is repeated at least 20 times in a genome, e.g., the human genome. In some embodiments, the set of primers is of a limited size and may contain at least 10, at least 20, at least 50, up to 100 or 200 primers. In some embodiments a set may contain 10 to 100 primers, although more or less primers can be used in some cases. In many embodiments, each primer of the set will have a 3' terminal sequence of at least 12 nucleotides (e.g., a 3' terminal sequence of at least 12, at least 15 or at least 18 nucleotides) that is complementary to a sequence that is repeated in a target genome. The 3' end of each primer can specifically hybridize to a sequence that is repeated at least 50, at least 100, at least 500, at least 1,000, at least 5,000 or at least 10,000 times in the genome, where the sequence to which a primer hybridizes should be on both strands of a chromosome, meaning that some instances of the sequence are found on the top strand of the chromosome and some instances of the sequence are found on the bottom strand of the chromosome. These primers are not random primers and they do not have a random sequence at the 3' end. The average distance between adjacent binding sites in genome for any primer in the set may be, independently, at least 2 kb, at least 5 kb, at least 10 kb, at least 50 kb or at least 100 kb. Specifically, the average distance between adjacent binding sites in the genome for a first primer in the set may be at least 2 kb, at least 5 kb, at least 10 kb, at least 50 kb or at least 100 kb, and the average distance between adjacent binding sites in the genome for a second primer in the set may be, independently, at least 2 kb, at least 5 kb, at least 10 kb, at least 50 kb or at least 100 kb, etc. The primers are not designed to amplify repeated regions (e.g., retrotransposon repeats) that are dispersed throughout the genome, and the amplification products do not comprise repeated regions.

Collectively, the set of primers can be designed to amplify at least 50 regions having a total length of at least 100 kb (meaning that the total amount of sequence amplified in the reaction can be at least 100 kb) in a polymerase chain reaction using, for example, a eukaryotic genome as a template. The number of regions amplified in the reaction (which corresponds to the number of amplicons produced by the reaction), the collective length of the regions amplified, and the length of the individual amplicons can be controlled by altering the number and sequences of the primers in the set. In some embodiments, the set of primers may collectively amplify at least 100, at least 500, at least 1,000, at least 5,000, or at least 10,000, up to 50,000 or more regions, depending on the primers used, the origin and type of the sample, and the conditions used. In some embodiments, the total length of the regions amplified in the reaction (which corresponds to the total length of the amplicons produced by the reaction), can have a total length of at least 10 kb, e.g., at least 50 kb, at least 100 kb, at least 250 kb, at least 500 kb, at least 1 Mb, at least 2 Mb up to 5 Mb or more, as desired. In some embodiments, the set of primers may be designed to amplify at least 500 regions (resulting in the same number of amplicons), e.g., 500 to 2,000 regions (or amplicons), covering at least 250 kb of the genome. In other embodiments, the set of primers may be designed to amplify at least 5,000 regions (or amplicons), e.g., 5,000 to 20,000 regions (or amplicons), covering at least 2.5 Mb of the genome. In any embodiment, the median length of the amplified regions (or amplicons) may be in the range of 100 bases to 500 bases.

FIG. 1 shows how one can amplify multiple regions from a section of a genome, where the number of regions amplified is greater than the number of primers used. This hypothetical example uses two primers (primers 1 and 2). Up to a point, the addition of each additional primer can result in the amplification of hundreds or thousands more regions. Since, in practice, many more than two primers can be used in the method (e.g., 10 to 100 primers, or up to 500) and a whole genome will be used as a template, thousands or tens of thousands of products can be amplified using tens of primers. In some cases, the number of distinct amplicons produced in a reaction may be at least of 5×, at least 10×, at least 100×, at least 500× or at least 1,000× the number of primers used in the reaction. In the hypothetical example shown in FIG. 1, there are two primers (primers 1 and 2), which hybridize to and are capable of priming DNA synthesis at a sequence that is repeated. In this example, primer 1 hybridizes to 8 sites (four on the top strand and four on the bottom strand), whereas primer 2 hybridizes to 5 sites (two on the top strand and three on the bottom strand). In this example, only four of the combinations primers are capable of generating an amplicon in a PCR reaction. These amplicons are indicated as amplicons 1-4. Other combinations of primers are unproductive because, e.g., the binding sites for the primers are too far way from one another or their binding sites are found on different fragments in the sample.

As shown, some of the amplicons (amplicons 1, 3 and 4) are amplified using both primers and, as such, those amplicons will have the sequence of primer 1 at one end and the sequence of primer 2 at the other. Other amplicons (amplicon 2) may be amplified by a single primer, thereby producing a product that has the same sequence at both ends. In some embodiments, some but not all (e.g., 20% to 80%, e.g., 40% to 60%) of the primers in the set may comprise a first 5' tail and the reminder of the primers in the set may comprise a second 5' tail, where the first and second 5' tails have different sequences. For example, primer 1 in the embodiment shown in FIG. 1 may comprise a first 5' tail whereas the primer 2 may comprise a second 5' tail, where the sequences of the tails are different. In these embodiments, at least some of the amplicons produced in an initial PCR reaction (i.e., the amplicons that are amplified using two primers such as amplicons 1, 3 and 4, but not amplicons that are amplified by one primer such as amplicon 2) can be sequenced directly or re-amplified by PCR using universal primers that hybridize to the 5' tails or their complements prior to sequencing. In other cases, some primers may include a 5' tail that varies in sequence, meaning that some molecules of the primer have a first 5' tail and other molecules have a second 5' tail. In this example, primers 1 and 2 may each have a 5' tail, where (i) approximately half of the molecules of primer 1 have one 5' tail and the remainder of the molecules of primer 1 have a different 5' tail, and (ii) the sequence of the 5' tail of primer 2 may be composed of two sequences, where approximately half of the molecules of primer 2 have one 5' tail and the remainder of the molecules of primer 2 have a different 5' tail. In this latter implementation, amplicon 2 can be amplified using universal primers along with amplicons 1, 3 and 4 because some molecules of amplicon 2 will have one tail sequence on one end and the tail sequence on the other end.

Figure 2:
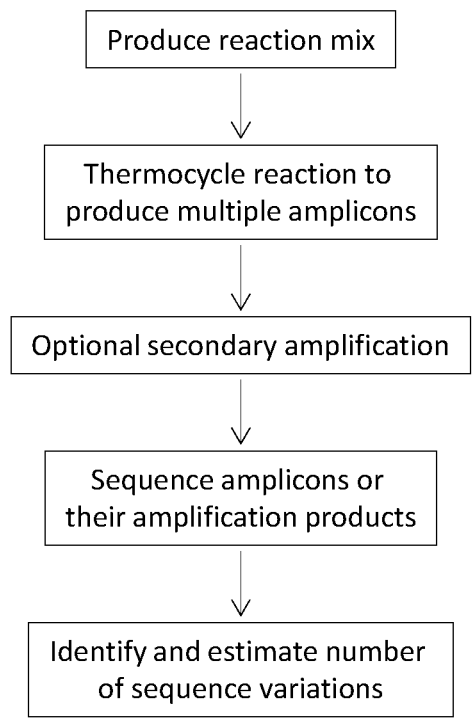
FIG. 2 schematically illustrates an exemplary workflow in which the present method could be employed.

FIG. 2 schematically illustrates an exemplary workflow by which the present method could be implemented.

Any tail and/or universal primer can include other informational sequences such as sample barcodes, index sequences, random sequences and/or replicate barcodes, as desired. As would be apparent, the tails of the primers and/or the universal primers may be compatible with use in the next generation sequencing platform used for sequence analysis, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps. Nanopore sequencing may be used in some embodiments.

Because the sequences of several thousand genomes are known, primer sets can be readily designed before use. In some embodiments, the primers can be designed using the following exemplary protocol, although other protocols could be used. In this example, sequences of a particular length (i.e., sequences that have the same length in the range of 12 to 40 bases) that are found in a reference genome can be sorted according to their abundance in the genome. For example, the abundance of each 18 mer sequence in the human genome can be calculated. The most abundant sequences are then selected. In the 18 mer example, one could select the top 2,000 18 mer sequences, where the most common 18 mer sequence is found 703,100 times in the human genome (which sequences are spaced apart by an average of about 2 kb) and the $2,000^{th}$ most common 18 mer sequence is found 15,145 times in the human genome (which sequences are spaced apart by an average of about 100 kb). Then sequences having a GC content of between 20% and 80% are selected (although sequences having a broader GC content can be used in some cases), since good primers often have a balanced GC content. Next, the sequences are compared to one another to determine which sequences that have a significant overlap with another sequence. This can be done by determining if any of the sequences is identical to another sequence over 8 or 10 nucleotides, particularly at the 3' end. If there is significant overlap between two sequences, then the less abundant sequence is eliminated. Next, the intervals (i.e., the distance, in nucleotides) between pairs of opposing sequences in the genome can be calculated, and the sequences of the regions between the opposing binding sites (i.e., the sequences of the predicted amplicons) can be analyzed. The least abundant sequences can be eliminated if some of the intervals are undesirably short (e.g., less than 1,000 nt, less than 500 nt, less than 200 nt, less than 100 nt, or less than 50 nt, as desired), and/or if the regions between the opposing binding sites overlap with one another, e.g., by at least 30%. The sequences of the predicted amplicons (i.e., the sequence between the opposing primers) can then be mapped back to the reference genome to ensure that the sequences accurately map back onto the reference genome (e.g., with a MAPQ score of >20 and up to 3 mismatches). The sequences of the predicted amplicons can be compared and primer sequences that result in the most unique amplicon sequences can be selected. A set of primers can then be designed using the selected primer sequences, where the 3' ends of the primers are the same as the selected sequences.

The combined length of the regions amplified by the primers can be altered in many different ways. For example, combined length of the regions amplified may be altered by changing the number of primers in the reaction. In some embodiments 10 to 100 primers can be used in an assay. However, the method may be performed using at least 4 and up to 500 or 100 primers in some cases. Further, if the primers hybridize to less prevalent sequences, then the lengths of the individual amplicons should increase which, in turn, can potentially result in the combined length of the amplified regions. For example, in the design method described above one could eliminate the first few hundred most abundant sequences in the first step of the exemplary method, thereby increasing the average distance between the primers. In some embodiments, set of primers can be designed such that the closest binding sites for the primers on opposite strands of the genome is no more than 1,000 nucleotides apart. This design should result in a product in which each amplicon is at least 1,000 bp in length. In some embodiments, the closest binding sites for opposing primers are in the range of 100-500 nucleotides apart. This design should result in a product in which the amplicons have a minimal length in the range of 100-500 nucleotides.

In some embodiments, the primers may be used to estimate the number of sequence variations in a sample of DNA. In these embodiments, the method may comprise combining the sample of DNA with a thermostable polymerase, dNTPs (e.g., dATP, dGTP, dTTP and dCTP) and a set of primers described above to produce a reaction mix, and then thermocycling the reaction mix. The reaction conditions may be readily adapted from to those used for PCR, e.g., may involve 3-40 cycles (e.g., 10-40 cycles) of that include a denaturation step at a temperature of over 90° C., e.g., at about 95° C., an annealing step at a temperature in the range of 50° C. to 75° C., and an extension step at a temperature of 70-75° C. Two step cycling may also be used. The polymerase used in the method can be any suitable thermostable polymerase such as Taq polymerase, VENT, and Phusion polymerase, etc., and, as would be apparent, necessary cofactors (e.g., $Mg^{2+}$, salt, and a buffering agent) should be present in the reaction. In some embodiments, the polymerase used in this step of the method should have a low error rate. In some embodiments, the polymerase may be a proofreading DNA polymerase, which typically have a 3' to 5' exonuclease activities. Examples of non-proofreading thermostable polymerases (i.e., thermostable polymerases that do not have a 3' to 5' exonuclease activity) include, but are not limited to Taq and Tth. Examples of proofreading thermostable polymerases include, but are not limited to, Pfu (Agilent Technologies, Santa Clara, CA), Pwo (Roche, Basel, Switzerland), Tgo (Roche, Basel Switzerland), VENT® (New England Biolabs, Ipswich, MA), DEEP VENT® (New England Biolabs, Ipswich, MA), KOD HiFi (Novagen, Madison, WI), PFX50™ (Invitrogen, Waltham, MA), HERCULASE II™ (Agilent Technologies, Santa Clara, CA), PLATINUM PFX™ (Life Technologies, Waltham, MA) and ProofStart™ (Qiagen, Hilden, Germany) These polymerases, on average, produce 4× to 8× fewer errors than Taq polymerase. Further examples of proofreading thermostable polymerases include, but are not limited to, PHUSION® (Thermo Fisher Scientific, Waltham, MA), PFUULTRA™ (Agilent Technologies, Santa Clara, CA), PFUULTRA™ II (Agilent Technologies, Santa Clara, CA), IPROOF™ (Bio-Rad, Hercules, CA), Q5 polymerase, and KAPAHIFI™ (Kapa Biosystems, Wilmington, MA). These polymerases, on average, produce at least 20× fewer errors than Taq polymerase and can be readily employed herein. Thermocycling the reaction mix results in a reaction product comprising at least 50 amplicons (e.g., at least 100, at least 500, at least 1,000, at least 5,000, or at least 10,000, up to 50,000 or more amplicons) having a total length of at least 100 kb (e.g., at least 250 kb, at least 500 kb, at least 1 Mb, at least 2 Mb up to 5 Mb or more, as desired).

Next, the amplicons produced by thermocycling the reaction, or amplification products thereof (if the amplicons are re-amplified by universal primers that hybridize to 5' tails in the primers) are sequenced to produce sequence reads. The sequencing step may be done using any convenient next generation sequencing method and may result in at least at least 100,000, at least 500,000, at least 1M at least 10M at least 100M, at least 1B or at least 10B sequence reads per reaction. In some cases, the reads may be paired-end reads.

The sequence reads are then processed computationally. The initial processing steps may include identification of barcodes (including sample identifiers or replicate identifier sequences), and trimming reads to remove low quality or adaptor sequences. In addition, quality assessment metrics can be run to ensure that the dataset is of an acceptable quality.

After the sequence reads have undergone initial processing, they are analyzed to identify which reads correspond to the target sequence (or a variant thereof). These sequences can be identified because they are identical or near identical to a target sequence (which correspond to sequences between opposing primers and are generated computationally using a reference genome). As would be recognized, the sequence reads that are identical or near identical to the target sequence can be analyzed to determine if there is a potential variation in the target sequence.

Next, the method may comprise (d) analysing the sequence reads to estimate the number of sequence variations in the amplified regions. In some cases, the sample may be known to contain a particular sequence variation and, as such, the sequence reads that correspond to the variant are readily identified. In other cases, a variation may identified de novo (e.g., using the method described by e.g., Forshew et al, Sci. Transl. Med. 2012 4:136ra68, Gale et al, PLoS One 2018 13:e0194630, Weaver et al, Nat. Genet. 2014 46:837-843, or another suitable method). Calling sequence variations in some samples (e.g., cell-free DNA) can be challenging because the variant sequences are generally in the minority (e.g., less than 10% of the sequence). As such, in some embodiments, the present method may comprise: (a) for each nucleotide position of a particular amplicon, determining, e.g., plotting, an error distribution that shows how often amplification and/or sequencing errors occur at different sequencing depths; (b) based on the distribution for each position of the sequence, determining a threshold frequency for each different sequencing depth at or above which a true genetic variation can be detected; (c) sequencing the sample to obtain plurality of reads for an amplicon; and determining, for each position of the amplicon, whether the frequency of a potential sequence variation in the sequence reads is above or below the threshold. Mutation may be identified (or "called") at a position if the frequency of sequence reads that contain the variation is above the threshold. A variation can also be called using an accumulation of evidence for the variation. In some cases, a variation may be called only if it occurs in multiple (e.g., two, three or four) replicates (i.e., in the same amplicon from multiple independent amplification reactions, amplified using different aliquots of same sample).

After the sequence variations have been identified, the total number of identified sequence variations can be counted. The total number of variations (or a score representing the same) provides an estimate of the number of sequence variations in the sample. If the subject is a pregnant female or an organ transplant patient (and if cell-free DNA is used as the sample), then the variations may derived from a developing fetus or transplanted organ. In these embodiments, the variations could be polymorphisms (e.g., single nucleotide polymorphisms, for example). In other embodiments, the subject may have cancer, and number of sequence variation in the sample provides an estimate of the mutational load of the sample. Since mutational load correlates with the patient's response to immunotherapy (e.g., treatment by an immune checkpoint inhibition such as by PD-1 or PD-L1 blockade, etc.) the total number of nucleotide variations in the sample (or a score representing the same) can be used to predict whether the patient will be susceptible to immunotherapy.

In some embodiments, the sample of DNA may be a sample of cfDNA from maternal blood. In these embodiments, the method may comprise sequencing the amplicons or amplification products thereof to produce sequence reads; and analysing the sequence reads to detect a foetal aneuploidy. This can be done by, e.g., counting sequence reads or molecular indexes, methods for which are known. For example, this embodiment may comprise detecting an increase in copy number of the amplicons amplified from chromosomes 21, 18 and/or 13, relative to reference region.

In other embodiments, the sample of DNA may be a sample of cfDNA from an organ transplant recipient. In these embodiments, the method may comprise detecting a change in copy number of amplicons amplified from DNA of the transplanted organ. DNA from the transplanted organ can be detected because it contains polymorphisms that are not in the recipient's genome. In these embodiments, an increase in the level of cfDNA that comes from the transplanted organ increases over time (e.g., to a level that is above a threshold) may indicate the transplanted organ is not healthy and an immunosuppressant (or more immunosuppressant, if the patient is already on it) may be administered to the patient.

As described above and below, the method can be used to determine if a patient is susceptible to immunotherapy. However, the method can also be applied to a number of other problems. For example, two further uses for the method are in copy number analysis and assessing size of cell free DNA. For example, in some embodiments the method may be used to assess other characteristics of DNA such as the quantification of different regions. As would be apparent, by comparing the number of sequencing reads present in test and reference regions of the genome one could detect changes in relative amounts of DNA for those regions. Examples may include gains of whole chromosomes such as trisomy 21 and focal changes such as the amplification of the MYC gene. In other embodiments this method may be used to analyze the distribution of fragment size in a sample comprising DNA fragments. In these embodiments, the primers may target a plurality of locations throughout the genome with a distribution of target product sizes. Primer pairs that target regions larger than the fragments in the same should not amplify and, as such, should be possible to detect the size of the fragments in a sample in a very sensitive way, as well as to detect small changes in the distribution of sizes of DNA. This could be used to determine if a blood sample had undergone white blood cell lysis and therefore any cell free DNA is contaminated with white blood cell DNA. It is known that cell free fetal DNA and ctDNA from certain cancers is shorter than typical cell free DNA thus, this method could be used for assessing foetal and tumor burden. The method may also be used to detect quality of DNA such as from FFPE. In addition, the method could be used to measure microsatellite instability (MSI), as the repetitive regions contain homopolymer stretches that could serve as markers of MSI. In addition, the method may be used to identify or measure mutational patterns rather than single variant. For example, a region may not map uniquely making it impossible to make a perfect call, but could still be used to estimate mutation load. In some embodiments, mutational burden may not be determined using specific calls and, in some embodiments, the method may allow for errors in order to identify patterns. In these embodiments, a particular variant need not be called with a high level of confidence or with any confidence at all. Rather, an overall number or pattern of mutations can be used instead.

In some embodiments, the sample of DNA used as a template in the reaction is a sample of cfDNA or a sample of DNA extracted from a tissue biopsy, where the term "tissue biopsy" is intended to refer to a sample of cancerous tissue taken from the body in order to examine it more closely. A biopsy may be from bone marrow, skin or from an internal organ and may be collected by an endoscopic biopsy (e.g., cystoscopy, bronchoscopy or colonoscopy), a fine needle aspiration, a core needle, or surgery for example.

The method described herein can be employed to analyze genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, where in certain embodiments the mammal is a human. In exemplary embodiments, the genomic sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human. In some embodiments, the sample analyzed may be a sample of cfDNA obtained from blood, e.g., from the blood of a cancer patient, a pregnant female or a transplant patient.

The sample may be from a patient that is suspected or at risk of having a disease or condition, and the results of the method may provide an indication of whether the patient, or fetus thereof, has the disease or condition. In some embodiments, the disease or condition may be a cancer, an infectious disease, an inflammatory disease, a transplant rejection, or a chromosomal defect such as a trisomy.

As noted above, in some cases the sample being analyzed using this method may be a sample of cfDNA obtained from blood, e.g., from the blood of a pregnant female. In these embodiments, the method may be used to detect potential abnormalities in the genome of the developing fetus (as described above) or to calculate the fraction of fetal DNA in the sample, for example. In other embodiments, the target sequence may be cancer-related.

In some embodiments, the method may comprise providing a report indicating the the number of sequence variations in the sample, e.g., the mutational burden of the sample. In some embodiments, a report may additionally list of approved (e.g., FDA approved) therapies for cancers that are associated with a high mutational burden. This information can help a physician to make treatment decisions.

In some embodiments, the method may involve administering immunotherapy to the subject if the number of sequence variations in the sample is above a threshold. In some embodiments, the method may comprise identifying a patient as having an estimated number of sequence variations that is above a threshold and administering an effective amount of the immunotherapy to the patient. For example, in some embodiments, an immune checkpoint inhibitor such as an antibody (which term is intended to include nanobodies, phage display antibodies, single chain antibodies, etc.) that binds to CTLA-4, PD1, PD-L1, TIM-3, VISTA, LAG-3, IDO or KIR, etc. may be administered to the patient if the number of sequence variations in the sample is above a threshold number, where the threshold can be empirically determined by determining the correlation between the number of sequence variations and the effectiveness of a treatment. The patient may have already been identified as having a tumor that is positive for one or more of the markers, CTLA-4, PD1, PD-L1, TIM-3, VISTA, LAG-3, IDO or KIR. In these embodiments, if a tumor is PD1, PD-L1 positive, and the number of sequence variations is above a threshold, then the method may involve administering an anti-PD1 or anti-PD-L1 antibody to the patient. The same principle can be applied to tumors that are positive for other markers. If the number of sequence variations in the sample is below the threshold, then the patient may not respond to immunotherapy and, as such an alternative therapy may be administered to the patient. In some cases, the alternative therapy may be a non-targeted therapy, i.e., a therapy that is not targeted to a particular sequence variation. Non-targeted therapies include radiation therapy, systemic or local chemotherapy, hormone therapy, immunotherapy (e.g., immune checkpoint inhibition) and surgery. Examples of systemic chemotherapies for non-small cell lung cancer and some other cancers include platinum-based doublet chemotherapy such as the combination of cisplatin and pemetrexed and the combination of cisplatin and gemcitabine. In other cases, the alternative therapy may be a therapy that is targeted to an actionable sequence variation, i.e., a therapy that targets the activity of the protein having a causative sequence variation, where the term "actionable sequence variation" is a sequence variation for which there is a therapy that specifically targets the activity of the protein having the variation. In many embodiments an actionable sequence variation causes an increase in an activity of the protein, thereby resulting in cells containing the variation to grow, divide and/or metastasize without check and in combination with other variations, such as in tumor suppressor genes, leading to cancer. Therapy that is targeted to an actionable sequence variation often inhibits an activity of the mutated protein. Examples of actionable sequence variations for non-small cell lung cancer and some other cancers, as well as therapies that target those actionable variations, are known. Targeted therapies directed against these activating alterations in EGFR, ALK, ROS1 and BRAF have been approved for use in patients harboring these activating mutations and fusions, and thus, these are described as "actionable" mutations, although others are known.

In some embodiments, the report may be in an electronic form, and the method comprises forwarding the report to a remote location, e.g., to a doctor or other medical professional to help identify a suitable course of action, e.g., to identify a suitable therapy for the subject. The report may be used along with other metrics to determine whether the subject is susceptible to a therapy, for example.

In any embodiment, a report can be forwarded to a "remote location", where "remote location," means a location other than the location at which the sequences are analyzed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet, including email transmissions and information recorded on websites and the like. In certain embodiments, the report may be analyzed by an MD or other qualified medical professional, and a report based on the results of the analysis of the sequences may be forwarded to the patient from which the sample was obtained.

In some embodiments, a biological sample may be obtained from a patient, and the sample may be analyzed using the method. In particular embodiments, the method may be employed to identify and/or estimate the mutation burden of the sample.

In some embodiments, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may indicate the presence and/or quantity of minority variant(s) in the sample. Once generated, the report may be forwarded to another location (which may be the same location as the first location), where it may be interpreted by a health professional (e.g., a clinician, a laboratory technician, or a physician such as an oncologist, surgeon, pathologist or virologist), as part of a clinical decision.

The results provided by this method may be diagnostic, prognostic, theranostic and, in some cases, may be used to monitor one or more mutations. In the latter embodiments, the levels of the sequence variations may be analyzed at multiple time points in the DNA from a patient. In some embodiments, a decrease in the levels of the variations (comparing between two or more time points) may indicate that a treatment is working and should therefore be continued. In some embodiments, an increase in levels of mutations identified by the method, may indicate that a treatment is not working and should therefore be modified or stopped.

In some embodiments, results obtained from the method may be used to guide treatment decisions. In these embodiments, the method may be a method of treatment comprising performing or having performed the method described above, and administering a treatment to the patient if an actionable copy alteration is identified.

As would be readily appreciated, many steps of the method, e.g., the sequence processing steps and the generation of a report indicating the amount of a target sequence or variant thereof in a sample may be implemented on a computer. As such, in some embodiments, the method may comprise executing an algorithm that calculates the amount of a target sequence or variant thereof based on the analysis of the sequence reads, and outputting a value indicating the amount. In some embodiments, this method may comprise inputting the sequences into a computer and executing an algorithm that can calculate the amount of a target sequence or variant thereof using the input sequences.

As would be apparent, the computational steps described may be computer-implemented and, as such, instructions for performing the steps may be set forth as programing that may be recorded in a suitable physical computer readable storage medium. The sequencing reads may be analyzed computationally.

EMBODIMENTS

Embodiment 1

A method for estimating the number of sequence variations in a sample of DNA from a subject, comprising:
(a) combining the sample of DNA with a thermostable polymerase, dNTPs and a set of primers to produce a reaction mix, wherein the 3' end of each primer specifically hybridizes to a sequence that is repeated at least 20 times in the genome of the subject;
(b) thermocycling the reaction mix to produce a reaction product comprising at least 50 amplicons having a total length of at least 100 kb;
(c) sequencing the amplicons of step (b) or amplification products thereof to produce sequence reads; and
(d) analysing the sequence reads to estimate the number of sequence variations in the regions amplified in step (b),
wherein the number of sequence variations identified in (d) provides an estimate of the number of sequence variations in the sample.

Embodiment 2

The method of embodiment 1, wherein the sequence variations are mutations.

Embodiment 3

The method of embodiment 1, wherein the sequence variations are polymorphisms.

Embodiment 4

The method of any prior embodiment, wherein the sample of DNA is a sample of cfDNA or a sample of DNA extracted from a tissue biopsy.

Embodiment 5

The method of any prior embodiment, wherein the subject has cancer and number of mutations in the sample provides an indication of tumor mutational burden.

Embodiment 6

The method of any prior embodiment, wherein the set of primers comprises at least 10 primers.

Embodiment 7

The method of embodiment 1, wherein the 3' terminal 12 nucleotides of each primer is repeated at least 50 times in the genome of the patient.

Embodiment 8

The method of embodiment 1, wherein the 3' terminal 12 nucleotides of each primer is repeated at least 100 times in the genome of the patient.

Embodiment 9

The method of embodiment 1, wherein the reaction product of step (b) comprises at least 500 amplicons covering at least 250 kb.

Embodiment 10

The method of embodiment 1, wherein the reaction product of step (b) comprises at least 5000 amplicons having a total length of at least 2.5 Mb.

Embodiment 11

The method of embodiment 1, wherein amplicons of (b) are less than 500 bases in length and reaction product comprising at least 200 amplicons.

Embodiment 12

A set of primers, wherein:
the 3' end of each primer specifically hybridizes to a sequence that is repeated at least 20 times in a eukaryotic genome, and
collectively, the set of primers amplifies at least 50 regions having a total length of at least 100 kb, in a polymerase chain reaction using the eukaryotic genome as a template.

Embodiment 13

The set of primers of embodiment 12, wherein the set of primers comprises at least 10 primers.

Embodiment 14

The set of primers of embodiments 12 or 13, wherein the 3' terminal 12 nucleotides of each primer is repeated at least 50 times in the genome of the patient.

Embodiment 15

The set of primers of any of embodiments 12-14, wherein the closest binding sites for the primers on opposite strands of the genome are no more than 1000 nucleotides apart.

Embodiment 16

The set of primers of any of embodiments 12-15, wherein the closest binding sites for the primers on opposite strands of the genome are in the range of 100-500 nucleotides apart.

Embodiment 17

The set of primers of any of embodiments 12-16, wherein the genome is the human genome.

Embodiment 18

The set of primers of any of embodiments 12-17, wherein the primers are in a mixture.

Embodiment 19

The set of primers of any of embodiments 12-18, wherein some but not all of the primers comprise a first 5' tail and the reminder of the primers comprise a second 5' tail.

Embodiment 20

A method for amplifying a sample, comprising:
(a) combining a sample of DNA with a thermostable polymerase, dNTPs and a set of primers of embodiment 12-19 to produce a reaction mix; and
(b) subjecting the reaction mix to thermocycling to produce a reaction product comprising at least 50 amplicons having a total length of at least 100 kb.

Embodiment 21

The method of embodiment 20, further comprising:
(c) sequencing the amplicons of step (b) or amplification products thereof to produce sequence reads; and
(d) analysing the sequence reads to identify sequence variations in the regions of the eukaryotic genome amplified in step (b).

Embodiment 22

The method of embodiment 21, further comprising (e) determining the number of sequence variations in the regions amplified in step (b).

Embodiment 23

The method of embodiments 21 or 22, wherein the sequence variations are mutations.

Embodiment 24

The method of any of embodiments 21-23, wherein the sequence variations are polymorphisms.

Embodiment 25

The method any of embodiments 20-24, wherein the sample of DNA is a sample of cfDNA or a sample of DNA extracted from a tissue biopsy.

Embodiment 26

The method of any of embodiments 22-25, wherein the number of mutations provides an indication of mutational burden.

Embodiment 27

A method for treating a patient with an immunotherapy comprising:
- (a) combining cell-free DNA (cfDNA) from the patient with a thermostable polymerase, dNTPs and a set of primers to produce a reaction mix, wherein the 3' end of each primer specifically hybridizes to a sequence that is repeated at least 100 times in the genome of the patient; and
- (b) thermocycling the reaction mix to produce a reaction product comprising at least 500 amplicons having a total length of at least 100 kb;
- (c) sequencing the amplicons of step (b) or amplification products thereof to produce sequence reads;
- (d) analysing the sequence reads to estimate the number of sequence variations in the regions amplified in step (b); and
- (e) administering an immunotherapy to the patient if the estimated number of sequence variations is above a threshold.

Embodiment 28

The method of embodiment 27, wherein the set of primers comprises at least 10 primers.

Embodiment 29

The method of embodiments 27 or 28, wherein the 3' terminal 12 nucleotides of each primer is repeated at least 500 times in the genome of the patient.

Embodiment 30

The method of any of embodiments 27-29, wherein the 3' terminal 12 nucleotides of each primer is repeated at least 1,000 times in the genome of the patient.

Embodiment 31

The method of any of embodiments 27-30, wherein the reaction product of step (b) comprises at least 1,000 amplicons covering at least 250 kb.

Embodiment 32

The method of any of embodiments 27-31, wherein the reaction product of step (b) comprises at least 10,000 amplicons having a total length of at least 2.5 Mb.

Embodiment 33

The method of any of embodiments 27-32, wherein amplicons of (b) are less than 500 bases in length.

Embodiment 34

The method of any of embodiments 27-33, wherein the immunotherapy is an immune checkpoint inhibitor.

Embodiment 35

The method of embodiment 34, wherein the immune checkpoint binds to CTLA-4, PD1, PD-L1, TIM-3, VISTA, LAG-3, IDO or KIR.

Embodiment 36

The method of any of embodiments 27-35, wherein the patient has non-small cell lung cancer (NSCLC), small cell lung cancer, bladder cancer, head and neck cancer, melanoma, renal cell carcinoma or a lymphoma.

Embodiment 37

The method of any of embodiments 27-36, wherein the method comprises identifying a patient as having an estimated number of sequence variations that is above a threshold and administering an effective amount of the immunotherapy to the patient.

EXAMPLES

Aspects of the present teachings can be further understood in light of the following example, which should not be construed as limiting the scope of the present teachings in any way.

Primer Design

To design primers, suitable candidates are identified by scanning the genome, and then filtered based on several criteria. Specifically, the following steps are undertaken:
- (a) K-mers identification: the fasta sequence of the genome (version hg38 in our case) is scanned for k-mers of fixed length (n=18 in our case, called 18-mers). The length of 18 is a compromise between having a high number of regions targeted and sufficient sequencing: we aim at selecting enough targets to allow pairing in close proximity for a sufficient number of regions, ideally to cover 1 Mb at depth >500 reads. 18-mers can be found in sufficient number in the genome while still providing sufficient stable hybridization to their respective target sequences. The jellyfish software (version >=2.27) is first used to scan the genome and generate the hits hash (command jellyfish count); then, the hash is processed to extract the top hits (command jellyfish dump). For practical reasons and to allow downstream processing to be computationally feasible, we limited this to the top 2,000 hits.
- (b) Bad k-mers removal: for each candidate primer, 18-mers with GC content outside of the 20-80% range or being the reverse complement of any other primer are removed; 18-mers overlapping more than 10% with others (command bedtools intersect) are also discarded as they are considered redundant.
- (c) Identify promising pairs: for each remaining primer, all possible pairs are inspected, and closely matching pairs are computed (command bedtools closest): only putative PCR products in the range of 50-114 nucleotides are considered. The reason behind this is that very little ctDNA above 150 nucleotides can be found and amplified, hence a target region length of 114=150-2*18 is set as the upper limit. Only primer pairs with more than 200 putative amplicons are retained as promising pairs.
- (d) Exclude overlapping pair regions: primer pairs amplified regions overlapping more than 30% with other regions (command bedtools intersect) are excluded as they would yield similar amplified regions.
- (e) Inspect uniqueness of amplified regions: target regions for each promising pair of 18-mers are extracted and aligned to the reference genome using the bwa mem aligner. Crucially, bwa mem is run with the "-a" parameter, which returns all mapping regions including secondary alignments. Only regions mapping to single locations with at most 3 mismatches and without indels are retained as unique alignments.

(f) Estimate covered area: for each primer pair, only primer pairs showing more than 90% of regions uniquely aligned are selected and the total region covered by all combination of all selected primer pairs is considered as the theoretical covered area. The effective covered area resulting from real experiments will diverge from this computational estimate as many factors can play a role in there, but this value can none the less be used to produce a relative indication of covered genome to rank primers, i.e. which primer pairs will cover and amplify more or less base pairs in the panel. The same primer sequences are then ordered as both forward and reverse from the list of selected primers.

Experimental

A total of 2 ng of cell free DNA (having a median size of approximately ~160 bp) was used. PCR amplification was performed using the primer panel (Table 1, which were designed using the above method). Each PCR reaction contained 25 uL DNA, 27.5 uL Platinum SuperFi 2× Master Mix (Invitrogen) and 2.5 uL of the primer pool. PCR cycling was as follows: 98C (30s), 5 cycles of (98C (10s), 70c (5 min), 72C (60s)), 72c (5 min). The PCR product was cleaned up using SPRIselect reagent (Beckman Coulter B23319) using the manufacturers protocol. DNA was eluted in 18 uL and a second PCR reaction using Indexed Illumina primers was performed (see table 2). Each PCR reaction contained 15 uL DNA, 17.5 uL Platinum SuperFi 2× Master Mix (Invitrogen) and 2.4 uL Indexed illumina primers. PCR cycling was as follows: 98C (30s), 14 cycles of (98C (10s), 62c (30s), 72C (60s)), 72c (5 min). The PCR product was cleaned up once using SPRIselect reagent (Beckman Coulter B23319) using the manufacturers protocol. Samples were pooled into a tube containing 10 uL 10 mM Tris-HCl pH 8. Samples were selected for 195-350 bp using a 2% Agarose Dye Free cassette and marker L on the Pippin Prep (Sage Science), following the manufacturer's instructions. Size selected DNA was quantified by qPCR using a KAPA Library quantification kit (KAPABIOSYSTEMS), following the manufacturer's instructions. Quantified libraries were sequenced on the NextSeq500 Illumina platform and data analysis was performed as below.

TABLE 1

Amplification Primers

```
Primer Sequence 5'-3'
TCGTCGGCAGCGTCAGATGTGTATAAGAGACAGAGCCTCCCAAGTAGCT
GG
(SEQ ID NO: 1)

TCGTCGGCAGCGTCAGATGTGTATAAGAGACAGCACTGCACTCCAGCCT
GG
(SEQ ID NO: 2)

TCGTCGGCAGCGTCAGATGTGTATAAGAGACAGCATTGCACTCCAGCCT
GG
(SEQ ID NO: 3)
```

TABLE 1-continued

Amplification Primers

```
TCGTCGGCAGCGTCAGATGTGTATAAGAGACAGCCCACCTCAGCCTCCC
AA
(SEQ ID NO: 4)

TCGTCGGCAGCGTCAGATGTGTATAAGAGACAGCTCAGCCTCCCAAAGT
GC
(SEQ ID NO: 5)

TCGTCGGCAGCGTCAGATGTGTATAAGAGACAGGGAGGCGGAGGTTGCA
GT
(SEQ ID NO: 6)

TCGTCGGCAGCGTCAGATGTGTATAAGAGACAGGGAGGTTGCAGTGAGC
CG
(SEQ ID NO: 7)

TCGTCGGCAGCGTCAGATGTGTATAAGAGACAGTACAGGCATGAGCCAC
CG
(SEQ ID NO: 8)

TCGTCGGCAGCGTCAGATGTGTATAAGAGACAGTGGAGGTTGCAGTGAG
CC
(SEQ ID NO: 9)

GTCTCGTGGGCTCGGAGATGTGTATAAGAGACAGAGCCTCCCAAGTAGC
TGG
(SEQ ID NO: 10)

GTCTCGTGGGCTCGGAGATGTGTATAAGAGACAGCACTGCACTCCAGCC
TGG
(SEQ ID NO: 11)

GTCTCGTGGGCTCGGAGATGTGTATAAGAGACAGCATTGCACTCCAGCC
TGG
(SEQ ID NO: 12)

GTCTCGTGGGCTCGGAGATGTGTATAAGAGACAGCCCACCTCAGCCTCC
CAA
(SEQ ID NO: 13)

GTCTCGTGGGCTCGGAGATGTGTATAAGAGACAGCTCAGCCTCCCAAAG
TGC
(SEQ ID NO: 14)

GTCTCGTGGGCTCGGAGATGTGTATAAGAGACAGGGAGGCGGAGGTTGC
AGT
(SEQ ID NO: 15)

GTCTCGTGGGCTCGGAGATGTGTATAAGAGACAGGGAGGTTGCAGTGAG
CCG
(SEQ ID NO: 16)

GTCTCGTGGGCTCGGAGATGTGTATAAGAGACAGTACAGGCATGAGCCA
CCG
(SEQ ID NO: 17)

GTCTCGTGGGCTCGGAGATGTGTATAAGAGACAGTGGAGGTTGCAGTGA
GCC
(SEQ ID NO: 18)
```

TABLE 2

2$^{nd}$ PCR Primers

```
Primer Sequence 5'-3'
AATGATACGGCGACCACCGAGATCTACACCTCTCTATTCGTCGGCAGCG
TC
(SEQ ID NO: 19)

AATGATACGGCGACCACCGAGATCTACACTATCCTCTTCGTCGGCAGCG
TC
(SEQ ID NO: 20)
```

TABLE 2-continued

2nd PCR Primers

AATGATACGGCGACCACCGAGATCTACACGTAAGGAGTCGTCGGCAGCGTC
(SEQ ID NO: 21)

AATGATACGGCGACCACCGAGATCTACACACTGCATATCGTCGGCAGCGTC
(SEQ ID NO: 22)

AATGATACGGCGACCACCGAGATCTACACAAGGAGTATCGTCGGCAGCGTC
(SEQ ID NO: 23)

AATGATACGGCGACCACCGAGATCTACACCTAAGCCTTCGTCGGCAGCGTC
(SEQ ID NO: 24)

AATGATACGGCGACCACCGAGATCTACACCGTCTAATTCGTCGGCAGCGTC
(SEQ ID NO: 25)

AATGATACGGCGACCACCGAGATCTACACTCTCTCCGTCGTCGGCAGCGTC
(SEQ ID NO: 26)

CAAGCAGAAGACGGCATACGAGATTCGCCTTAGTCTCGTGGGCTCGG
(SEQ ID NO: 27)

CAAGCAGAAGACGGCATACGAGATCTAGTACGGTCTCGTGGGCTCGG
(SEQ ID NO: 28)

CAAGCAGAAGACGGCATACGAGATTTCTGCCTGTCTCGTGGGCTCGG
(SEQ ID NO: 29)

CAAGCAGAAGACGGCATACGAGATGCTCAGGAGTCTCGTGGGCTCGG
(SEQ ID NO: 30)

CAAGCAGAAGACGGCATACGAGATAGGAGTCCGTCTCGTGGGCTCGG
(SEQ ID NO: 31)

CAAGCAGAAGACGGCATACGAGATCATGCCTAGTCTCGTGGGCTCGG
(SEQ ID NO: 32)

CAAGCAGAAGACGGCATACGAGATGTAGAGAGGTCTCGTGGGCTCGG
(SEQ ID NO: 33)

CAAGCAGAAGACGGCATACGAGATCAGCCTCGGTCTCGTGGGCTCGG
(SEQ ID NO: 34)

To analyze the data, the following analytical steps were employed:

(a) Raw data pre-processing: raw reads are first processed by the clipper algorithm to identify and remove primer sequences from the list of primers in the panel. This algorithm ensures that correct primers are identified at both extremes of the read, by allowing minor divergences in the exact sequence through a dynamic programming based approach. Following this, reads are trimmed to remove low quality sequencing tails using the software sickle. Finally, reads from the two sequencing reads (read-1 and read-2 from paired-end sequencing) are merged into a single consensus read using the software flash, in order to reduce error rates.

(b) Reads alignment: merged reads are aligned using the bwa mem alignment software, with parameters equal to those used for the eTAM-seq workflow processing.

(c) Clean-up alignments: during alignment post-processing, only high-quality alignments are retained. Those alignments exhibit a quality of alignment (MAPQ score) above 40, no alternative alignments associated for the read (XA tag in the SAM format) and number of mismatches in the alignment less or equal than 3 (NM tag in the SAM format).

(d) Identifying regions of interest: coverage is computed from clean alignment files, and only contiguous regions with read depth above a certain threshold (e.g., 150) are considered. It is important to notice that more amplicon pairs can contribute to the read pileups at each region: an amplicon information table is prepared by analysing all the reads in each selected region.

(e) Identifying variation in the amplified regions: starting from the amplicon table information, only amplicon pairs with a substantial amount of reads (e.g., more than 5% of the read pileup total) are retained.

(f) Variant annotation and SNP filtering: multiple sequence alignments are computed for each amplicon in a given region, and the variant count table is computed. Tables for different amplicons on the same region are summed up and combined together. Common SNPs are filtered out from the variant list using SNP databases, such as the gnomad DB (Genome Aggregation Database).

(g) Repetitive regions filtering: variants mapping to regions with low complexity (e.g., TTTTTT, TTTATTT or TATATA) are filtered out as they likely result from sequencing and analytical artefacts. To compute sequence complexity, we used a customized algorithm that compresses the DNA string and calculates the compressed string size, similarly to file compression in common operating systems. The more the DNA string gets compressed, the lower is the sequence complexity (i.e., we are in presence of a repetitive sequence).

(h) Variant calibration and calling: different variants are calibrated by analyzing control plasma samples (CPLs) from a large number (>20) of healthy individuals. In this way, the background occurrence frequency of each mutation in each genomic location is pre-computed and a variant-specific likelihood model of background noise is estimated for each variant. Variant calling is performed with a statistical model that takes into account multiple available samples and the relative position of each measured variant frequency compared to its own background model.

Figure 3:
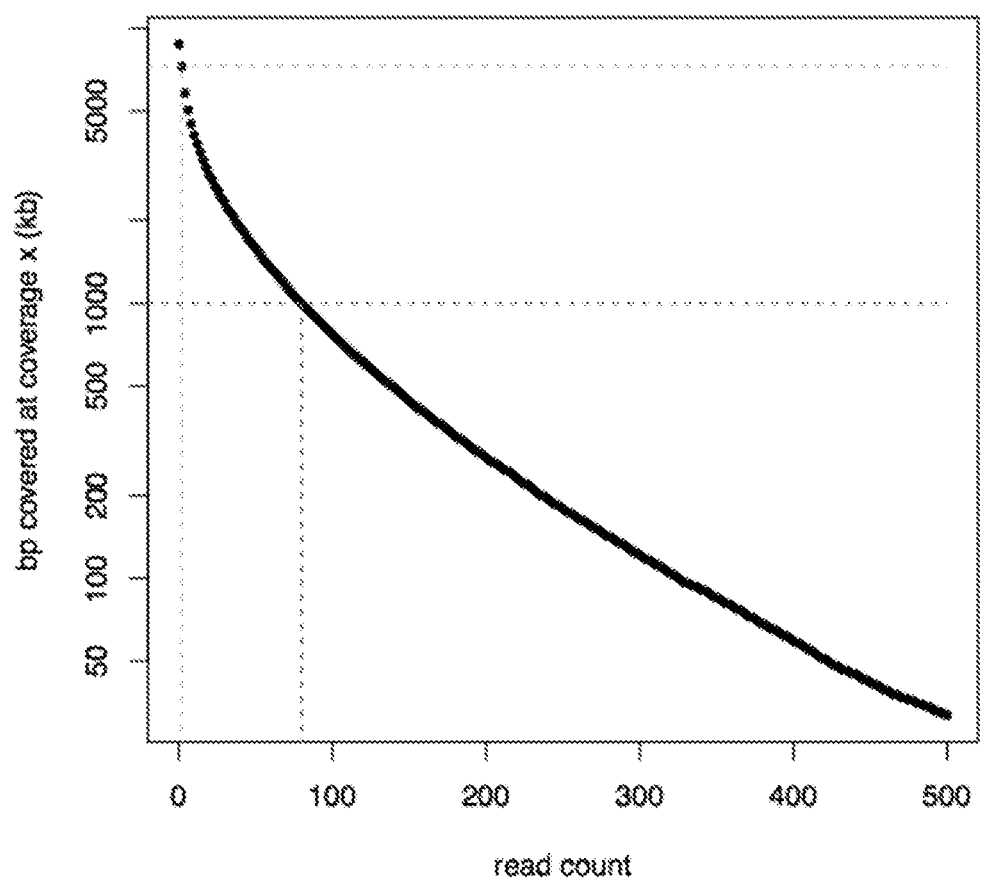
FIG. 3: is a graph showing read count vs kb covered. This graph shows that over 5 Mb of the genome can be amplified from cfDNA using 18 primers.

The results of this experiment are shown in FIG. 3. This data shows that at least 5 Mb of the genome human genome can be amplified using 18 primers.

What is claimed is:

1. A method for amplifying a sample, comprising:
   (a) combining a sample of cfDNA from the blood of a human with a thermostable polymerase, dNTPs and a set of at least 10 primers to produce a reaction mix, wherein:
      (i) the 3' end of each primer specifically hybridizes to a sequence that is repeated at least 20 times in the human genome,
      (ii) the binding sites for the primers on opposite strands of the human genome have a median interval in the range of 50-114 nucleotides; and
      (iii) collectively, the set of primers amplifies at least 50 regions having a total length of at least 100 kb, in a polymerase chain reaction using the human genome as a template; and
   (b) subjecting the reaction mix to thermocycling to produce a reaction product comprising at least 50 amplicons having a total length of at least 100 kb.

2. The method of claim 1, further comprising:
   (c) sequencing the amplicons of step (b) or amplification products thereof to produce sequence reads; and
   (d) analysing the sequence reads to identify sequence variations in the regions of the human genome amplified in step (b).

3. The method of claim 2, further comprising (e) determining the number of sequence variations in the regions amplified in step (b).

4. The method of claim 2, wherein the sequence variations are mutations.

5. The method of claim 2, wherein the sequence variations are polymorphisms.

6. The method of claim 1, further comprising:
   (c) sequencing the amplicons of step (b) or amplification products thereof to produce sequence reads; and
   (d) analysing the sequence reads to identify copy number variations in the regions of the human genome amplified in step (b).

7. The method of claim 1, wherein the sample of DNA is a sample of cfDNA from maternal blood.

8. The method of claim 7, wherein the method comprises:
   (c) sequencing the amplicons of step (b) or amplification products thereof to produce sequence reads; and
   (d) analysing the sequence reads to detect a foetal aneuploidy.

9. The method of claim 8, wherein the method is done by detecting an increase in copy number of the amplicons amplified from chromosomes 21, 18 and/or 13, relative to a reference region.

10. The method of claim 1, wherein the human is an organ transplant recipient.

11. The method of claim 10, wherein the method comprises detecting a change in copy number of amplicons amplified from cfDNA from the transplanted organ.

12. The method of claim 1, wherein the 3' terminal 12 nucleotides of each primer are repeated at least 50 times in the human genome.

13. A set of at least 10 primers, wherein:
   the 3' end of each primer specifically hybridizes to a sequence that is repeated at least 20 times in the human genome,
   the binding sites for the primers on opposite strands of the human genome have a median interval in the range of 50-114 nucleotides; and
   collectively, the set of primers amplifies at least 50 regions having a total length of at least 100 kb, in a polymerase chain reaction using the human a genome as a template,
   wherein some but not all of the primers comprise a first 5' tail and the reminder of the primers comprise a second 5' tail.

14. The set of primers of claim 13, wherein the 3' terminal 12 nucleotides of each primer are repeated at least 50 times in the human genome.

15. The set of primers of claim 13, wherein the primers are in a mixture.

* * * * *